(12) United States Patent
Ebersbach et al.

(10) Patent No.: US 11,399,714 B2
(45) Date of Patent: Aug. 2, 2022

(54) DEVICE FOR RELIABLY DETERMINING BIOMETRIC MEASUREMENT VARIABLES OF THE WHOLE EYE

(71) Applicant: Carl Zeiss Meditec AG, Jena (DE)

(72) Inventors: Ralf Ebersbach, Schmölin (DE); Martin Hacker, Jena (DE); Gerard Antkowiak, Jena (DE); Peter Klopfleisch, Jena (DE); Ferid Bajramovic, Mamming (DE); Tobias Bühren, Ulm (DE); Matthias Reich, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 0 days.

(21) Appl. No.: 16/913,308

(22) Filed: Jun. 26, 2020

(65) Prior Publication Data

US 2020/0345228 A1    Nov. 5, 2020

Related U.S. Application Data

(63) Continuation of application No. 15/583,439, filed on May 1, 2017, now Pat. No. 10,694,941, which is a
(Continued)

(30) Foreign Application Priority Data

Sep. 28, 2012    (DE) .................... 10 2012 019 474.9

(51) Int. Cl.
*A61B 3/107* (2006.01)
*A61B 3/10* (2006.01)
*A61B 3/117* (2006.01)

(52) U.S. Cl.
CPC .............. *A61B 3/107* (2013.01); *A61B 3/102* (2013.01); *A61B 3/1005* (2013.01); *A61B 3/1173* (2013.01)

(58) Field of Classification Search
CPC ......... A61B 3/10; A61B 3/1005; A61B 3/102; A61B 3/1035; A61B 3/107; A61B 3/117; A61B 3/1173; A61B 3/14
(Continued)

(56) References Cited

U.S. PATENT DOCUMENTS 5,585,873 A    12/1996 Shalon
6,779,891 B1 *  8/2004 Barth .................. A61B 3/1005
                                                      351/205
(Continued)

FOREIGN PATENT DOCUMENTS

DE        2 65 553 A1    3/1989
DE      196 36 472 A1    3/1998
(Continued)

OTHER PUBLICATIONS

DE Search Report (7 pages) with English translation (5 pages) for DE 10 2012 019 474.9 dated Oct. 30, 2014.
(Continued)

*Primary Examiner* — Ephrem Z Mebrahtu
(74) *Attorney, Agent, or Firm* — DeWitt LLP (57) ABSTRACT

A device for determining biometric variables of the eye, as are incorporated in the calculation of intraocular lenses including a multi-point keratometer and an OCT arrangement. The keratometer measurement points are illuminated telecentrically and detected telecentrically and the OCT arrangement is designed as a laterally scanning swept-source system with a detection region detecting the whole eye over the whole axial length thereof. The multi-point keratometer ensures that a sufficient number of keratometer points are available for measuring the corneal surface. By contrast, telecentricity ensures that the positioning inadequacies of the measuring instrument in relation to the eye to be measured do not lead to a local mismatch of the reflection points.

(Continued)

The swept-source OCT scan detects the whole eye over the length thereof so that both anterior chamber structures and retina structures can be detected and a consistent whole eye image can be realized.

11 Claims, 5 Drawing Sheets

Related U.S. Application Data continuation of application No. 14/431,450, filed as application No. PCT/EP2013/070199 on Sep. 27, 2013, now Pat. No. 9,649,027.

(60) Provisional application No. 61/707,004, filed on Sep. 28, 2012.

(58) Field of Classification Search
USPC .................................. 351/200–206
See application file for complete search history.

(56) References Cited

U.S. PATENT DOCUMENTS

| | | | |
|---|---|---|---|
| 7,322,699 B2* | 1/2008 | Barth | A61B 3/1005 351/205 |
| 7,452,077 B2 | 11/2008 | Meyer et al. | |
| 2004/0066489 A1 | 4/2004 | Benedikt et al. | |
| 2005/0057723 A1 | 3/2005 | Wakil et al. | |
| 2005/0203422 A1 | 9/2005 | Wei | |
| 2006/0158612 A1 | 7/2006 | Polland et al. | |
| 2007/0279586 A1 | 12/2007 | Jethmalani et al. | |
| 2008/0055543 A1* | 3/2008 | Meyer | A61B 3/113 351/205 |
| 2009/0161090 A1* | 6/2009 | Campbell | A61B 3/107 356/3 |
| 2009/0175525 A1 | 7/2009 | Farrer et al. | |
| 2009/0273757 A1 | 11/2009 | Merz et al. | |
| 2011/0102802 A1 | 5/2011 | Izatt et al. | |
| 2011/0157552 A1 | 6/2011 | Bublitz et al. | |
| 2012/0013849 A1* | 1/2012 | Podoleanu | A61B 3/1005 351/221 |
| 2012/0083667 A1* | 4/2012 | Isogai | A61B 3/14 600/300 |
| 2012/0092616 A1 | 4/2012 | Peyman | |
| 2012/0140174 A1 | 6/2012 | Hee et al. | |
| 2012/0184846 A1 | 7/2012 | Izatt et al. | |
| 2012/0200827 A1* | 8/2012 | Kato | G01B 9/02004 351/221 |
| 2012/0265181 A1* | 10/2012 | Frey | A61B 3/1035 606/5 |
| 2012/0303009 A1 | 11/2012 | Liu et al. | |

FOREIGN PATENT DOCUMENTS

| | | |
|---|---|---|
| DE | 10 2008 063 225 A1 | 7/2010 |
| DE | 10 2010 051 281 A1 | 5/2012 |
| WO | WO 2012/098194 A1 | 7/2012 |

OTHER PUBLICATIONS

PCT Notification of Transmittal of the International Search Report and the Written Opinion of the International Searching Authority, PCT International Search Report and PCT Written Opinion for PCT/EP2013/070199, dated Dec. 4, 2013, 9 pages.

Ultrahigh speed 1050 nm swept source/Fourier domain OCT retinal and anterior segment imaging at 100,000 to 400,000 axial scans per second, Optics Express, vol. 18, No. 19, pp. 20029-20048, (2010).

Application and File History for U.S. Appl. No. 14/431,450, filed Mar. 26, 2015. Inventors: Ralf Ebersbach et al.

Application and File History for U.S. Appl. No. 15/583,439, filed Sep. 27, 2013. Inventors: Ralf Ebersbach et al.

\* cited by examiner

DEVICE FOR RELIABLY DETERMINING BIOMETRIC MEASUREMENT VARIABLES OF THE WHOLE EYE

CROSS-REFERENCE TO RELATED APPLICATIONS

This application is a continuation of application Ser. No. 15/583,439, filed May 1, 2017, entitled "Device for Reliably Determining Biometric Measurement Variables of the Whole Eye", which is a continuation of application Ser. No. 14/431,450, filed Mar. 26, 2015, entitled "Device for Reliably Determining Biometric Measurement Variables of the Whole Eye", now U.S. Pat. No. 9,649,027 issued May 16, 2017, which is a national stage entry priority of PCT Application No. PCT/EP2013/070199, filed Sep. 27, 2013, which claims priority to German Patent Application No. 10 2012 019 474.9, filed Sep. 28, 2012, and also claims priority to U.S. Provisional Application No. 61/707,004, filed Sep. 28, 2012, each of which is hereby fully incorporated herein by reference.

TECHNICAL FIELD

The present invention relates to a device for determining biometric variables of the eye, as are incorporated in the calculation of intraocular lenses. Such variables are the radii—including the orientation thereof—of the corneal front side and the corneal rear side, asphericity of the cornea, thickness of the cornea—in the center or else as one- or two-dimensional profile—, anterior chamber depth, lens thickness, radii of the lens front side and/or rear side, axis length of the eye, in general the position and shape of the optically effective interfaces or the areas relevant optically to the visual faculty of the eye such as corneal front/rear sides, lens front side and rear side, retina in the eye. These variables or some of these variables are required for calculating intraocular lenses—referred to below as IOL calculation—in accordance with known IOL equations or by means of ray tracing methods.

BACKGROUND

The prior art has only disclosed OCT (optical coherence tomography) systems and topography/OCT combined systems for measuring the biometric variables of the whole eye. Although Scheimpflug, PCI (partial coherence interference) and topography systems or combined instruments of same measure some of the aforementioned variables, these combinations cannot measure all parameters of the eye. In particular, it is not possible to measure the lens rear side and the retina, or the respective profile of these areas, since these systems, even in a combined system, are restricted to measuring the anterior chamber and the axial one-dimensional length of the eye.

Only OCT systems with anterior and posterior chamber measurements of the eye and topography/OCT systems, likewise with posterior and anterior chamber measurement, are able to measure the whole eye.

A further possible combination is a combination of topography/Scheimpflug system for the anterior chamber measurement and an OCT system for the posterior chamber measurement. However, since the OCT can also detect the anterior chamber, the gain from the Scheimpflug anterior chamber measurement is low compared to the additional costs.

Compared to the topography/OCT combined systems, pure OCT systems are disadvantageous in that measuring the topography of the cornea by means of conventional topometers (in particular Placido systems) is substantially more accurate than the measurements of the OCT systems which are influenced by movement artifacts. Although said OCT systems can reduce these movement artifacts by faster measurements or by measurements which are registered to the eye, this is only possible with significant outlay and not readily possible in a reliable enough manner.

By way of example, a combination of Placido topographs and time domain B-scan OCT is described as topography/OCT combined system in US2004/066489. In principle, this allows the whole eye to be measured biometrically. However, the described device exhibits some significant disadvantages, which reduce the reliability of the measurement values.

Although Placido topography has a very high resolution, it is less reproducible in terms of reconstructing the surface when compared to keratometer measurements. This is due, firstly, to the assumptions made during the reconstruction of the topography in order to achieve the high resolution and/or in the lacking telecentricity/insufficient focusability of many topography systems compared to keratometers, and so positioning errors of the measurement instrument in relation to the patient become relevant during the topography measurement.

Furthermore, Placido topographs do not allow so-called Skrew rays to be taken into account, which are always generated in the case of the Placido ring illumination when the cornea is curved not only in a central plane through the corneal vertex but also in a plane perpendicular thereto, i.e. if it has azimuthal curvature. As a result of not taking this into account, the corneal surface is not reproduced correctly. Thus, overall, a Placido topograph does not reproduce the radius or, in general, the front side of the cornea reliably enough as required for the IOL calculation.

Furthermore, time-domain OCT systems are too slow and competitively priced spectrometer-based systems do not have the axial resolution and/or have a too small axial scanning or detection depth such that the eye length does not occur with the resolution required for the IOL calculation or such that there are only partial depth measurements. However, whole-eye biometrics, i.e. establishing the areas of the whole eye optically relevant to the visual faculty of the eye in terms of their position and their profile in the eye, are, in principle, possible in both cases by separate measurement of the anterior and posterior chamber and subsequent synthesis of the data, but the registration of the images to one another is often unreliable due to lack of a suitable common reference variable in the segment images.

Therefore, the Placido time-domain OCT system does not allow all biometric data to be obtained in a sufficiently reliable and simple manner for the IOL calculation.

A combination of a simple keratometer and a B-scan OCT is described as a topography/OCT combined system in US20050203422. This system also allows important biometric variables of the biometrics of the eye to be determined. However, the described device also exhibits some significant disadvantages, which reduce the reliability of the measurement values or leaves open important points which are relevant to whole-eye biometrics:

The described keratometer merely allows the robust measurement of the radii on the front side of the cornea. A higher-order description of the corneal surface or a description with a higher resolution than that of the described keratometer is not possible. However, this is increasingly required for the calculation of intraocular lenses (abbreviated IOLs), in particular for toric IOLs.

Furthermore, this does not solve the problem of assigning the topography measured by the keratometer to the spatial data from the OCT data, nor does it ensure that the OCT measurements are taken particularly quickly in order to compensate for the eye movement during the measurement.

SUMMARY

The present invention is based on the object of disclosing a device which measures measurement values for the biometric variables at the eye in a quick, reliable and reproducible fashion and with the required accuracy and resolution, which biometric variables are relevant to the calculation of intraocular lenses, also to those calculations which assume whole-eye biometrics.

In particular, the areas of the whole eye which are optically relevant to the visual faculty of the eye should be determined in terms of their position and their profile in the eye, which is referred to as whole-eye biometrics below. Here, the aforementioned variables are in the foreground, but it is also possible to use the device to extract different variables of the eye, which have not been used up until now, from the measurement data, in particular also those variables which are required for simulating an optical model of the eye.

The device for measuring biometric variables of the eyes for calculating intraocular lenses, consisting of a multi-point keratometer and an OCT arrangement, achieves this object by virtue of the fact that the multi-point keratometer is configured such that the keratometer measurement points are illuminated telemetrically and detected telecentrically and that the OCT arrangement is designed as a laterally scanning swept-source system with a detection region detecting the whole eye over the whole axial length thereof.

The multi-point keratometer ensures that, firstly, a sufficient number of keratometer points are available for measuring the corneal surface with a high resolution, but that the density of the measurement points is low enough for it to be possible to detect the Skrew rays. By contrast, the telecentricity ensures that the positioning inadequacies of the measurement instrument in relation to the eye to be measured do not lead to a local mismatch of the reflection points.

What the swept-source OCT scan, which captures the whole eye over the length thereof, achieves is that both anterior chamber and retina structures can be detected in the A-scan or B-scan and hence an orientation on the basis of the retina and the anterior chamber/cornea becomes possible during the scan. This makes it easier to combine the A- and/or B-scans to form a consistent whole-eye image. Here, the swept-source OCT is better than other OCT variants, such as time domain OCTs or spectrometer-based OCTs, in ensuring fast, movement artifact-free measurement of the A-scan over the whole eye length.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The device according to the invention for measuring biometric variables of the eye for calculating intraocular lenses consists of a multi-point keratometer and an OCT arrangement, wherein the multi-point keratometer is configured such that the keratometer measurement points are illuminated telecentrically and detected telecentrically and that the OCT arrangement is designed as a laterally scanning swept-source system with a detection region detecting the whole eye over the whole axial length thereof.

Figure 1:
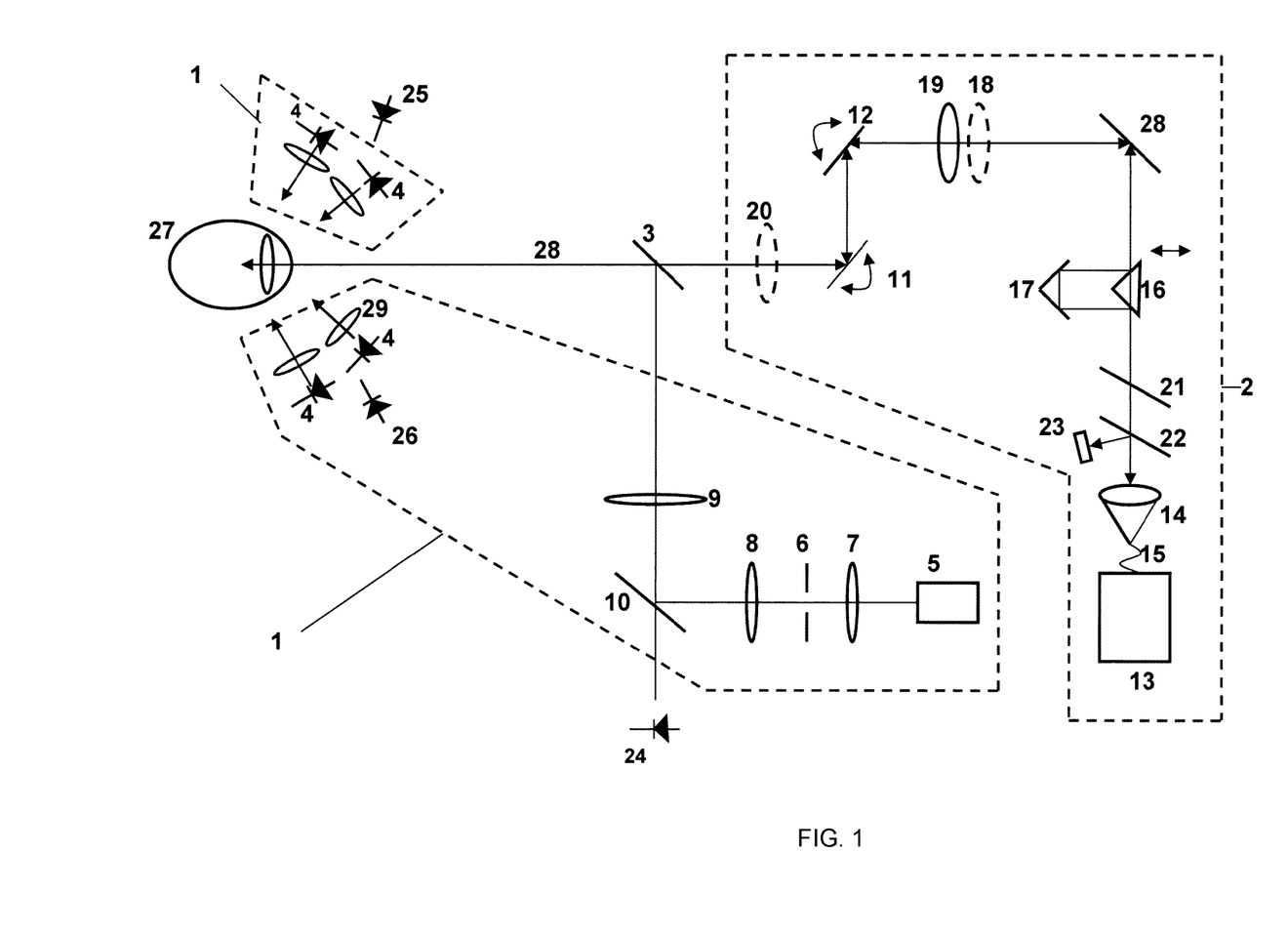
FIG. 1 depicts a basic optical design of an example embodiment the device.

FIG. 1 shows a basic optical design of the device: by means of the beam splitter 3, an OCT system 2 is unified with a multi-point keratometer system 1 on a common instrument axis 28 such that both can biometrically measure the eye 27 in a laterally assignable manner.

Here, the multi-point keratometer system 1 consists of several light sources, preferably LEDs 4, at different radial distances from the instrument axis 28. Lens attachments 29 ensure that the LEDs telecentrically illuminate the cornea in punctiform fashion by collinear beams. The beams reflected by the cornea are detected by a camera 5, upstream of which a telecentricity aperture 6 has been attached.

Instead of individual LEDs with an attachment lens, collimated light beams can alternatively be produced by appropriately designed Fresnel lenses, so-called fraxicons, using one or a few LEDs. This is particularly advantageous if very many mutually spaced apart collimated light beams are intended to be produced.

The telecentric design of the illumination and of the detection reduces the sensitivity with respect to positioning errors. This is because as a result of the telecentricity, only rays whose angle in relation to the cornea is known and which are independent of distance contribute to building up the image. Therefore this design ensures a higher reproducibility of the measurement of variables such as the corneal radius than in the case of a Placido topographer and hence the design is more reliable for obtaining IOL determination relevant parameters than a Placido topographer.

In a first embodiment, the keratometer illuminates and measures an angle corresponding to that of the keratometer of the IOLMaster by Carl Zeiss Meditec AG at 6 measurement points, which are arranged on a ring around the instrument axis, in particular at an illumination angle of between 17 and 18 degrees with respect to the instrument axis. This ensures that effects due to different angular alignments do not have to be taken into account when comparing measurement data from the IOLMaster and from the device according to the invention.

In a further embodiment, the keratometer illuminates and measures at several points which are distributed on several rings around the instrument axis. Here, at least 12 points which are arranged symmetrically around the instrument axis on at least 2 rings are preferred.

Figure 3:
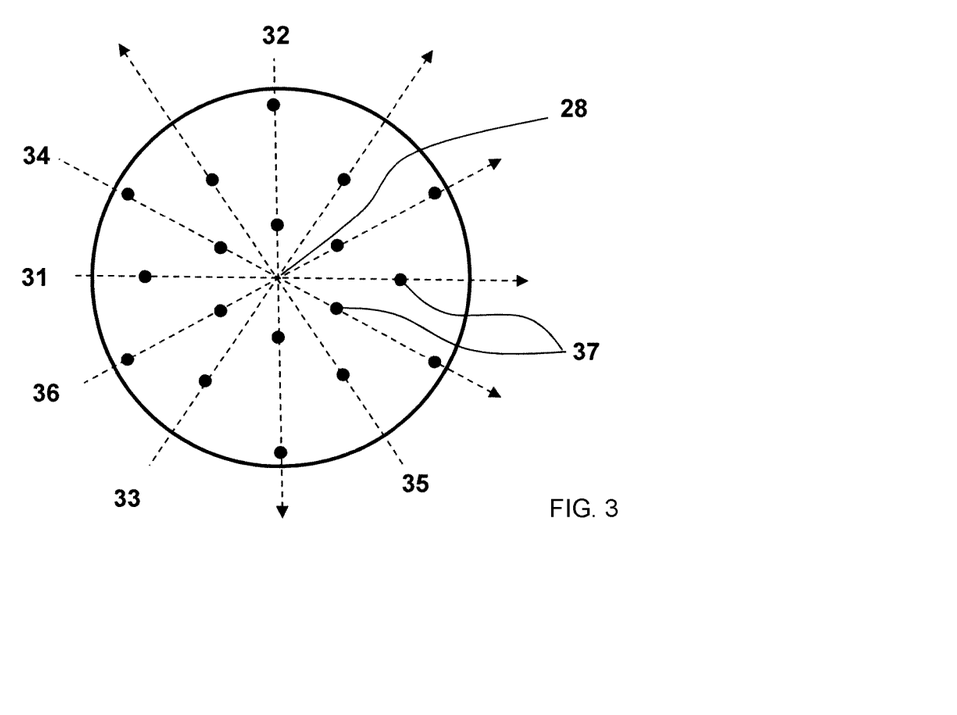
FIG. 3 depicts an example embodiment of the B-scan/keratometer geometry of the device.

Here, an arrangement with 3 rings with 6 points each is particularly preferred. To this end, FIG. 3 shows a possible arrangement. What the 3 ring arrangement ensures is that essential variables of the description of a corneal surface are measured, which variables are expedient for the IOL calculation of current IOLs to a good approximation: corneal radius, astigmatism or the 2 main radii and the position of the axis for one of the radii, corneal asphericity. What the rotation of the points of the first and the third rings in relation to the position of the points of the second ring, as shown in FIG. 3, achieves in particular is that the measurement points lie in regions at which a Zernike description of the corneal surface at a low order would expect the largest deviations compared to a spherical surface for many eyes. Furthermore, a geometry like in the IOLMaster keratometer can also be provided for the keratometer illumination of one of the rings in this case.

Here, the scanning direction of the OCT arrangement is preferably aligned in such a way that at least one B-scan of the OCT runs through at least one keratometer measurement point.

In order to supply an even higher resolution for a refined resolution of the corneal surface or for the more precise diagnosis of eye disorders, the keratometer illuminates and measures at more than 30 but less than 4000 keratometer measurement points, wherein the keratometer points are distributed on several rings or at least cover several regions radially. As a result, it is possible to determine higher orders of the corneal surface. However, in contrast to Placido topographs, a gap-free measurement of the corneal surface in conjunction with the OCT measurement is not expedient so as to enable the detection of so-called Skrew rays. Therefore a keratometer with more than 800 and less than 1600 measurement points is particularly preferred. This provides a good application-oriented compromise between topography resolution and the detectability of Skrew rays.

The necessity for taking Skrew rays into account is explained below:

What the use of a keratometer with several separate measurement points instead of a Placido topograph ensures is that even so-called Skrew rays are correctly taken into account when evaluating the local curvatures. This is particularly important because the local curvature of the cornea is important for the refraction of the OCT measurement beam into the cornea and hence into the eye. Errors in the curvature, in particular those which deflect the OCT beam out of the nominal meridian plane of the B-scan, lead to an erroneous positioning of the intraocular interfaces appearing in the B-scan. What is particularly serious in this case is that although the angle error in the refraction may be small, the positioning error connected therewith increases with increasing intraocular distance.

Figure 4:
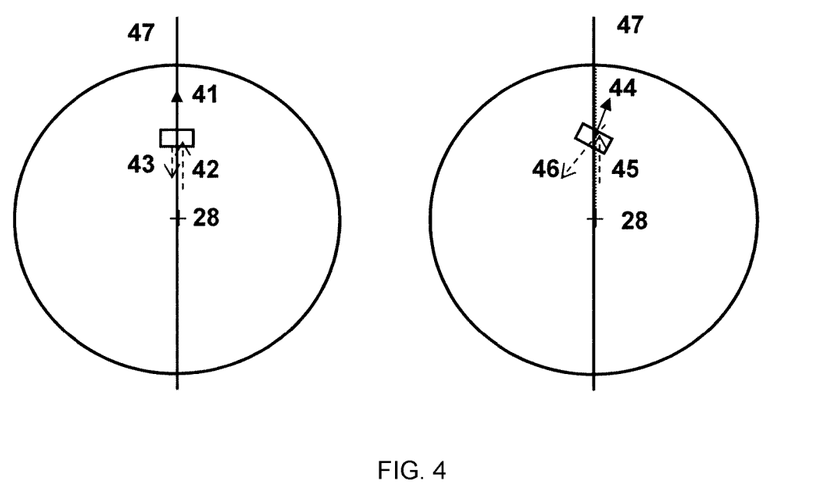
FIG. 4 illustrates the effect of Skrew rays when measuring the topography and in the case of OCT measurements.

This is illustrated in FIG. 4. The left-hand side of FIG. 4 shows a surface element of the cornea, which is only tilted radially. The vector area 41 therefore does not have an azimuthal component. Hence the OCT beam 42 which impinges on the corneal surface element as OCT beam 43 is also only refracted in the meridional plane. The right-hand side shows a surface element 44, which is also tilted in the azimuthal direction. This tilt is not detected by a conventional Placido or ring-projection system since the reflections out of the meridional plane superpose on reflections of other, neighboring corneal regions and the two components cannot be readily separated. By contrast, a multi-point keratometer is able to detect this since the reflection point on a detector of the keratometer appears outside of the meridional plane and—provided the illumination points are not situated very close together—no reflections from other illumination points interfere there. However, this tilt of the surface element now leads to an OCT beam 45, which falls onto the surface element with vector area 44, likewise being refracted out of the meridional plane as OCT beam 46. Hence an intraocular interface in the A-scan will likewise not lie in the meridional plane, but to the side thereof. Hence, without detecting this azimuthal tilt, the intraocular interface will be reproduced erroneously for forming a model of the eye.

In order to obtain a better assignability of the detected keratometer points to the associated illumination sources, it is advantageous for the keratometer in an additional embodiment if the keratometer points are sequentially illuminated and measured, either individually or in groups. This is particularly advantageous in the case of 2 or more groups of keratometer measurement points which in each case measure a majority of the corneal surface, and wherein the respective corneal areas overlap completely or to a large extent, but the keratometer points of the groups are in each case offset or rotated with respect to one another. As a result, for the measurement of one group, this ensures that the distance between two points of the group is large enough to achieve a reliable association between illumination source and detected spot but that the cornea can nevertheless still be measured with a high resolution by measuring various groups of keratometer measurement points. Thus, for example, in the case of an 18 point keratometer, the measurement can take place with 3 sub-groups, each with 6 points.

Furthermore, in an example embodiment as per FIG. 3, at least one or more B-scans 31 to 36 of the OCT pass through one or more of the keratometer illumination points 37. This is particularly advantageous if keratometer data of the corneal surface should be combined with intraocular distances, obtained by OCT, to form a whole-eye model for the IOL calculation by means of ray tracing. Aligning the B-scans at the keratometer measurement points ensures that, when composing data of the corneal front side from the keratometry and the intraocular data from the OCT, the OCT data are measured at the same position as the reflections from the corneal front side in the keratometer.

In so doing, the keratometer and OCT can be measured simultaneously with the help of a dichroic separation—to this end, the beam splitter 3 in FIG. 1 has a dichroic design—or simultaneously by removing the OCT illumination spot detectable in the keratometer image by software or alternately/sequentially in time with a little time delay (i.e. under a slight shift due to the eye movement). Alternatively, each of the two modalities can also be recorded separately, either simultaneously or in the same time-window with an iris and/or pupil and/or sclera image and be positioned laterally with respect to one another on the basis of said image. These types of separation of the OCT signal from the keratometer signal are not restricted to a keratometer but can also be applied to a Placido topograph instead of a keratometer.

In a further example embodiment—likewise depicted in FIG. 3—the B-scans of the OCT do not only pass through the keratometer points 37 but also form pairs, the scanning planes of which, e.g. 31 and 32, are respectively perpendicular to one another, wherein the various pairs are rotated with respect to one another in order to cover as many keratometer points as possible or all keratometer points.

An advantage of this is that, as per U.S. Pat. No. 7,452,077, a corneal vertex is determined for each pair and this vertex can be compared to the vertex of the cornea, as determined from the keratometer measurement. If the distance of the OCT vertex and the keratometer vertex varies too strongly during a sequence of OCT and keratometer measurements, this is an indication that the patient is not properly fixed and that the assignment of the OCT scans to the keratometer measurement points is not reliable enough for producing an eye model from keratometer and OCT data.

The following text describes the OCT system, with which the multi-point keratometer is advantageously combined for the biometric measurement/detection of the whole eye.

In accordance with FIG. 1, the OCT system consists of a swept-source interferometer 13, a collimator 14, at least one laterally deflecting scanner 11 and/or 12 and several optical elements or lenses, 18, 19 and 20, which serve to fix the focus plane of the OCT in the eye. The swept-source interferometer itself is sketched in 2 variants in FIGS. 5a and b. Here, this is a Mach-Zehnder arrangement in both cases, but other arrangements are also feasible.

As mentioned at the outset, swept-source systems are particularly suitable for recording whole-eye OCT scans due to the high sensitivity thereof. In particular, it is advantageous to satisfy the conditions as described in DE 10 2008 063 225 in the combination instrument. Here, an OCT wavelength of, for example, between 780 nm and 1100 nm, or in another example between 1010 nm and 1090 nm should also be selected for the application since light of these wavelengths is not perceived by the patient eye and can still penetrate well through eye lenses made opaque by the cataract. Within the scope of a combined instrument, a wavelength of 680-980 nm or greater than 1100 nm lends itself to be selected for the keratometer for the purposes of color separation.

Furthermore, the reliability of the obtained OCT signals can be improved in a further embodiment if, in addition to the sample interferometer, a reference interferometer is present for monitoring the laser wavelength during the sweep.

Figure 5A:
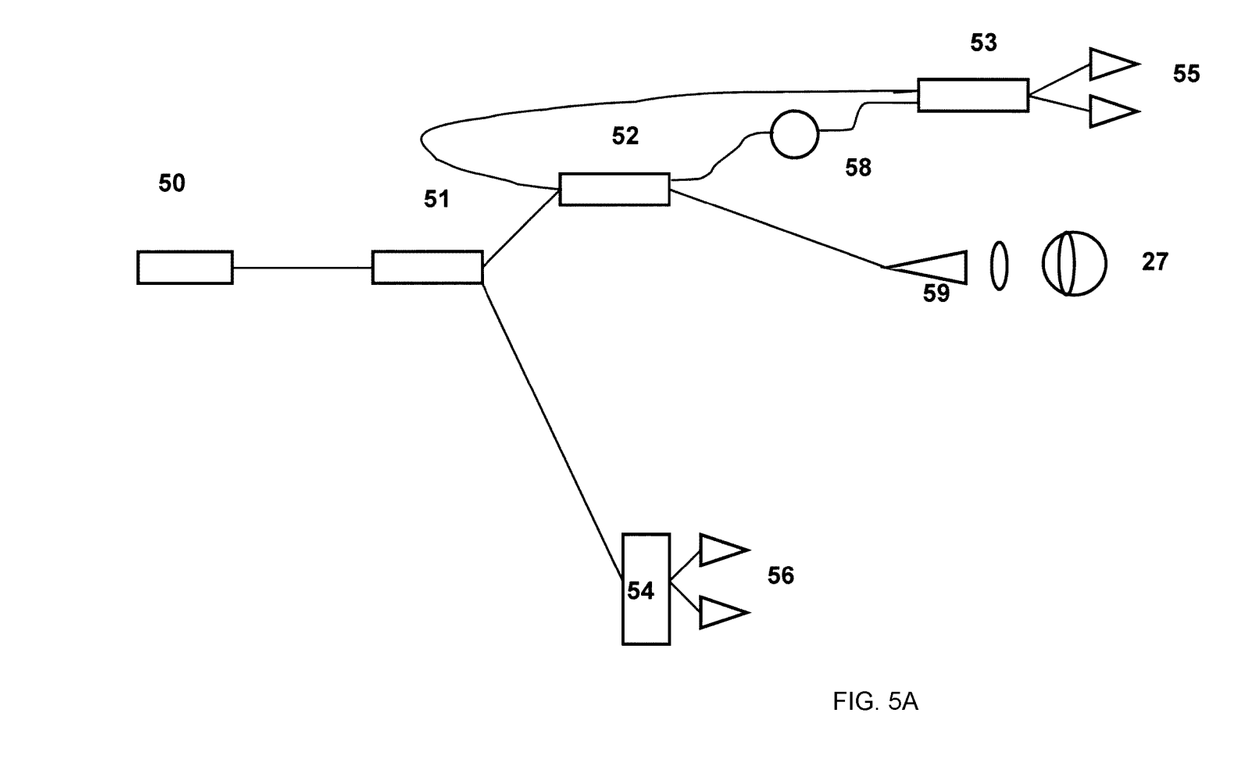
FIGS. 5a and 5b depict two embodiments of the basic design of an example swept-source OCT measurement system.
Figure 5B:
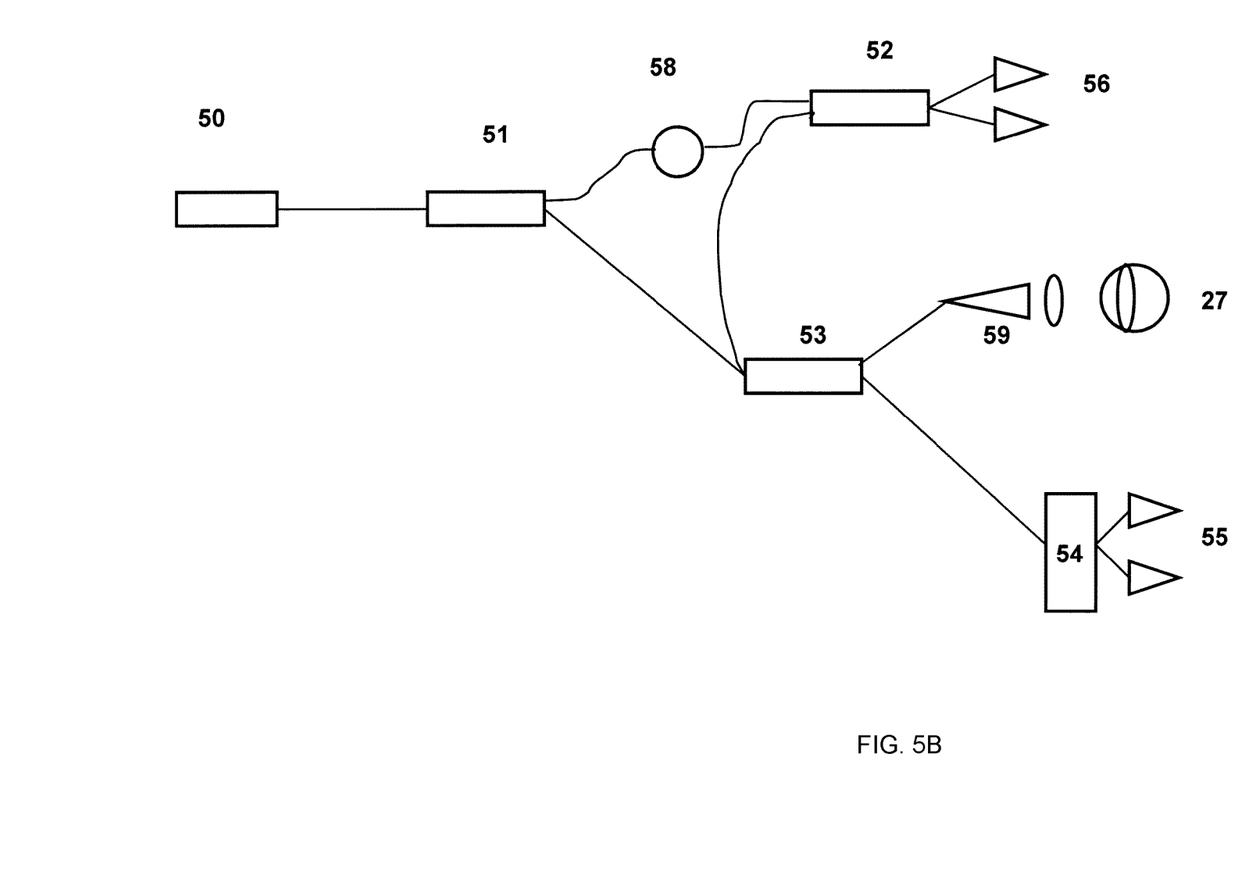

In this respect, FIG. 5A shows a specific design of a swept-source OCT system. Here, the light for the reference interferometer is decoupled directly after the light source or before the optical elements which are required for the actual sample measurement and sample referencing. An advantage of this is that the reference interferometer can be integrated into a swept-source laser module. Alternatively, FIG. 5B shows an arrangement in which this reference interferometer does not lie immediately in the light source itself or does not lie in front of the optical elements which are required for the actual sample measurement and sample referencing, but rather lies thereafter.

In another example embodiment, a switch is undertaken between a retina mode and an anterior chamber mode by means of a delay line. In the case of the retina mode, the focus of the OCT illumination beam and the zero point of the coherence gate are set in the vicinity of the retina. The zero point of the coherence gate is in this case preferably set behind the retina. Furthermore, the point of rotation during the B-scan lies in the eye pupil such that, as in the case of a pure retina OCT, a B-scan/cross-sectional recording of the retina is brought about with a high lateral and axial resolution. In the case of the anterior chamber mode, the focus of the OCT illumination beam and the zero point of the coherence gate lie near or in the anterior chamber. It is particularly preferable for the focus to lie in the anterior chamber and for the zero point of the coherence gate to lie in front of the cornea. Furthermore, the point of rotation lies—virtually—in the vicinity of the retina such that the B-scan supplies a high-resolution cross-sectional image of the anterior chamber, as is known from anterior chamber OCTs.

Figure 2A:
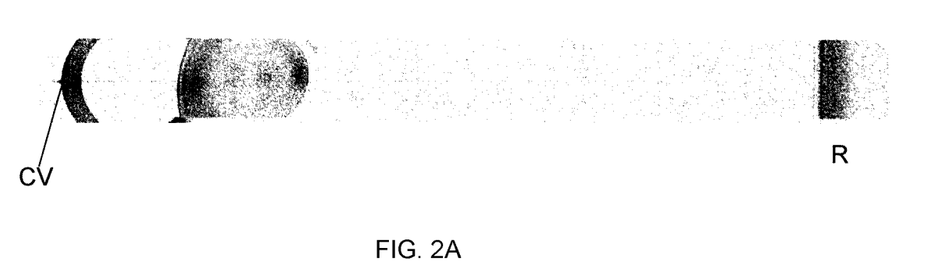
FIGS. 2a and 2b depict two B-scans, which are recorded in different OCT measurement modes: in an anterior chamber mode and in a retina mode respectively.
Figure 2B:
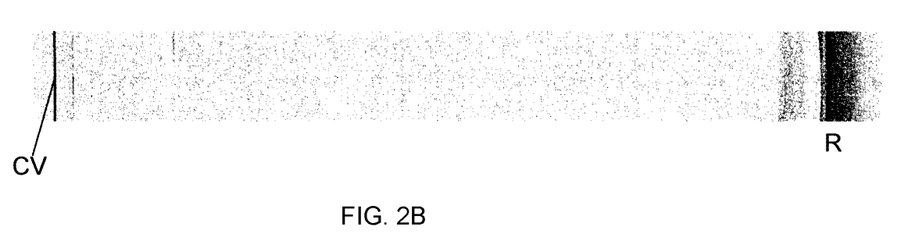

However, a high sensitivity of the swept-source OCT ensures in both scan modes that the part of the eye that is not in focus is also available as a signal. This is shown in FIGS. 2a and 2b. In the anterior chamber mode depicted in FIG. 2a, the signal from the retina R is also present, albeit not with a high lateral resolution. In the retina mode depicted in FIG. 2b, the signal from the corneal front side CV is also present. Hence, the A-scan, which in each case takes place along the main instrument axis—and which is the same as the visual axis of the patient which is aligned by a fixing light—, can link the B-scans of both modes to one another axially and compensate for axial movements of the eye between 2 scans in different modes. In principle, the detection of one common interface is sufficient, but it is often unclear in an interface signal as to what interface this actually is. Here, in the various modes, 2 interface signals per scan supply a better assignability to the interfaces in the eye.

In a further example embodiment, the delay line is extended in the anterior chamber mode compared to the retina mode by further optical elements. This happens so that fewer optical elements of the measuring instrument are in the beam path in the case of the retina mode such that the lower retina signal is not further attenuated by reflections at optical elements of the instrument. By contrast, for the stronger signals from the anterior chamber—due to higher refractive index changes and fewer optical elements of the eye in the measurement beam path compared to signals from the retina—the attenuation of the signal by reflections at the focus-shifting and delay line-shifting optical units can be tolerated. An embodiment is described in FIG. 1, in which the switch to the anterior chamber mode is achieved by pivoting in the lens 18, tipping away the lens 20 and inserting the prism 16.

In a further embodiment, the device has one or more LEDs for illuminating the eye and/or the close surroundings thereof. In FIG. 1, only LED 25 of these LEDs is shown in an exemplary manner. A recording by the image sensor of the keratometer then supplies an image which is used for lateral positioning of the instrument in relation to the eye or for determining the distance from limbus to limbus. In this case, it is advantageous if, in contrast to the keratometer measurement, there is a change in the focus position for focusing on the surroundings of the eye by pivoting lenses in and/or out. The lateral positioning of the instrument by means of surrounding image can be complemented by axial positioning using an OCT measurement in the anterior chamber mode.

In a further embodiment, the device has one or more LEDs for illuminating the sclera. In respect of the emitted wavelengths, these are selected for good contrast of the blood vessels and/or the iris. In FIG. 1, only LED 26 of these LEDs is shown in an exemplary manner. A recording by the image sensor of the keratometer then supplies an image which enables the lateral and rotational registration of the OCT and/or multi-point keratometer measurement values in relation to the eye. This registration can be used for forming an eye model from the measurement values or for the subsequent intraoperative alignment of an intraocular lens.

All elements and embodiments described in the explanations above contribute in their totality to increasing the speed, reliability, robustness and accuracy of the measurement of biometric variables, as are required for calculating intraocular lenses.

Not all aspects are necessarily used for a different measurement object. By way of example, if an instrument should only measure a cross section of the anterior chamber and the axis length of the eye, it is sufficient in a combined instrument of multi-point keratometer and anterior chamber OCT for only the anterior chamber to be detected by the OCT rather than the whole eye. Then the OCT need not cover the whole eye and it is then advantageously possible to combine other OCT systems, such as time-domain and spectrometer-based systems, with the multi-point keratometer. This is because all these OCT/multi-point keratometer systems profit from taking the Skrew rays into account for obtaining data for the corneal surface, which then in turn are used for the lateral localization/assignment of the OCT data.

LIST OF REFERENCE SIGNS

1 Keratometer system
2 OCT system
3 Beam splitter
4 LED
5 Camera, area sensor
6 Telecentricity aperture
7, 8 Lenses for setting the foci
9 Objective lens
10 Beam splitter
11, 12 Pivotable mirrors
13 OCT interferometer
14 Collimator
15 Optical waveguide
16 Insertable prism
17 Beam deflection
18, 19, 20 Lenses for setting the foci and the field
21 Shutter
22 Beam splitter
23 Photodiode power measurement
24 Fixing LED
25 Surrounding illumination LED
26 Sclera illumination LED
27 Eye
28 Instrument axis
29 Attachment lens
28 Instrument axis
31-36 B-scan directions
37 Keratometer illumination measurement points
41, 44 Surface element vectors
42, 45 Incident OCT beam
43, 46 OCT beam optically refracted at the surface element
47 OCT scanning and corneal central plane
50 Swept-source source
51, 52, 53 Couplers
54 Reference interferometer
55, 56 Balanced detectors
58 Path length adaptation
59 Collimator at the interferometer
CV Corneal front side
R Retina Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A device for measuring biometric variables of eyes for calculating intraocular lenses, comprising:
   a multi-point keratometer; and
   an optical coherence tomography (OCT) arrangement:
      wherein the multi-point keratometer comprises keratometer measurement points and wherein the keratometer measurement points are illuminated telecentrically in punctiform fashion by collimated beams and detected telecentrically;
      wherein the OCT arrangement comprises a laterally scanning swept-source system with a detection region detecting a whole eye over a whole axial length of the eye; and
      wherein the OCT arrangement is configured to switch between an anterior chamber measurement mode and a retina measurement mode such that OCT data is obtained in the anterior chamber measurement mode and/or in the retina measurement mode, and wherein each of the anterior chamber measurement mode and/or the retina measurement mode is adapted to the respective eye segment to be measured in respect of a focal position or a coherence gate; and wherein in the anterior chamber measurement mode a signal from a retina is also present and in the retina measurement mode a signal from an anterior surface of a cornea is also present.

2. The device as claimed in claim 1, wherein the multi-point keratometer comprises at least 12 keratometer measurement points arranged in an annular fashion in at least two rings.

3. The device as claimed in claim 1, wherein the multi-point keratometer comprises at least 18 keratometer measurement points arranged in an annular fashion in 3 rings with 6 keratometer measurement points each ring.

4. The device as claimed in claim 1, wherein the multi-point keratometer comprises more than 30 but less than 4000 keratometer measurement points.

5. The device as claimed in claim 1, wherein the multi-point keratometer comprises more than 800 but less than 1600 keratometer measurement points.

6. The device as claimed in claim 1, wherein at least 2 B-scans, which are perpendicular to one another, are performed by the OCT arrangement.

7. The device as claimed in claim 1, wherein in the case of the retina measurement mode, a focus of an OCT illumination beam and a zero point of the coherence gate are set in a vicinity of the retina.

8. The device as claimed in claim 7, wherein the zero point of the coherence gate is set behind the retina.

9. The device as claimed in claim 1, wherein in a case of the anterior chamber measurement mode a focus of an OCT illumination beam and a zero point of the coherence gate lie near or in an anterior chamber.

10. The device as claimed in claim 9, wherein the focus lies in the anterior chamber and the zero point of the coherence gate to lies in front of the cornea.

11. The device as claimed in claim 1, wherein a measuring light emitted by the OCT arrangement has a wavelength of between 1010 and 1090 nm.

* * * * *

UNITED STATES PATENT AND TRADEMARK OFFICE
CERTIFICATE OF CORRECTION

| | | |
|---|---|---|
| PATENT NO. | : 11,399,714 B2 | Page 1 of 1 |
| APPLICATION NO. | : 16/913308 | |
| DATED | : August 2, 2022 | |
| INVENTOR(S) | : Ebersbach et al. | |

It is certified that error appears in the above-identified patent and that said Letters Patent is hereby corrected as shown below:

On the Title Page

In Item (72), under "Inventors", Column 1, Line 1, delete "Schmölin (DE);" and insert --Schmölln (DE);--

In the Specification

Column 1, Line 9, delete "2017," and insert --2017, now U.S. patent No. 10,694,941, issued Jun. 30, 2020,--

Column 1, Line 32, delete "profile--," and insert --profile,--

Column 1, Line 48, delete "PCI (partial coherence interference)" and insert --PCI (partial coherence interferometry)--

Column 2, Line 29, delete "Skrew rays" and insert --Skew rays--

Column 2, Line 62, delete "biometrics:" and insert --biometrics.--

Column 3, Line 33, delete "telemetrically" and insert --telecentrically--

Column 3, Line 41, delete "Skrew rays." and insert --Skew rays.--

Signed and Sealed this
Twenty-fourth Day of December, 2024

Derrick Brent
*Acting Director of the United States Patent and Trademark Office*